(12) United States Patent
Kealey et al.

(10) Patent No.: US 6,372,267 B1
(45) Date of Patent: *Apr. 16, 2002

(54) FOODS CONTAINING COCOA SOLIDS HAVING HIGH COCOA POLYPHENOL CONTENTS

(75) Inventors: Kirk S. Kealey, Lancaster; Rodney M. Snyder, Elizabethtown, both of PA (US); Leo J. Romanczyk, Jr., Hackettstown, NJ (US); John F. Hammerstone, Jr., Nazareth, PA (US); Margaret M. Buck, Morristown; Giovanni G. Cipolla, Alpha, both of NJ (US)

(73) Assignee: Mars Incorporated, Mclean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/470,394

(22) Filed: Dec. 22, 1999

Related U.S. Application Data

(63) Continuation of application No. 08/709,406, filed on Sep. 6, 1996, now Pat. No. 6,015,913.

(51) Int. Cl.[7] ............................ A61K 35/78; A23L 1/36; A23L 1/10; A23L 1/216
(52) U.S. Cl. ................ 424/776; 426/631; 426/481; 426/482
(58) Field of Search .......................... 424/195.1, 776; 426/631, 481, 482

(56) References Cited

U.S. PATENT DOCUMENTS

| | | | | |
|---|---|---|---|---|
| 4,704,292 A | * | 11/1987 | Kattenberg | 426/593 |
| 5,405,633 A | * | 4/1995 | Heidlas et al. | 426/442 |
| 5,554,645 A | * | 9/1996 | Romanczyk et al. | 514/453 |
| 5,776,536 A | * | 7/1998 | Tremblay et al. | 426/660 |
| 6,015,913 A | | 1/2000 | Kealey et al. | 549/386 |
| 6,066,350 A | * | 5/2000 | Purtle et al. | 426/430 |

FOREIGN PATENT DOCUMENTS

| | | |
|---|---|---|
| DE | 19544905 | 5/1997 |
| JP | 7-213251 | 8/1995 |
| JP | 7-274894 | 10/1995 |
| JP | 9-206026 | 8/1997 |
| JP | 9-224606 | 9/1997 |
| JP | 9-234018 | 9/1997 |
| WO | WO 96/10404 | * 4/1996 |

OTHER PUBLICATIONS

Ziegleder et al., "Antioxidative effects of Cocoa", *CCB*, vol. 8, No. 4 pp. 3–6 (1983).

* cited by examiner

*Primary Examiner*—Christopher R. Tate
(74) *Attorney, Agent, or Firm*—Margaret B. Kelley, Esq.; Clifford Chance Rogers & Wells, LLP

(57) ABSTRACT

The present invention is directed to a method of processing a fat-containing bean, e.g., cocoa beans, for producing solids comprising active polyphenols and/or fat-containing products, comprising extracting the fat to produce solids and fat-containing products. Additionally, the inventive method also provides cocoa compositions comprising at least one active polyphenol, wherein the concentration of the polyphenol(s) with respect to the nonfat solids is conserved with respect to the concentration of the active polyphenol(s) in the bean from which the compositions are derived.

19 Claims, 5 Drawing Sheets

Column: Supelcosil LC-SI 4.6mm X 250mm, 5mm
Detector: FLD, Ex=276 Em=316
Column Temperature: 37°C
Mobile Phase: A-Methylene Chloride    B-Methanol    C-50/50 $H_2O$/HOAc
Flow Rate: 1 ml/min

| Gradient: | Time | %A | %B | %C |
|---|---|---|---|---|
| | 0 | 82 | 14 | 4 |
| | 30 | 67.6 | 28.4 | 4 |
| | 60 | 46 | 50 | 4 |

```
Column: Supelcosil LC-SI 4.6mm X 250mm, 5mm
Detector: FLD, Ex=276 Em=316
Column Temperature: 37°C
Mobile Phase:  A-Methylene Chloride    B-Methanol    C-50/50 H2O/HOAc
Flow Rate:     1 ml/min Gradient:      Time      %A      %B      %C
               0         76      20      4
               25        46      50      4
               30        10      86      4
```

FOODS CONTAINING COCOA SOLIDS HAVING HIGH COCOA POLYPHENOL CONTENTS

CROSS-REFERENCE TO RELATED APPLICATIONS

This application is a continuation of Ser. No. 08/709,406 filed Sep. 6, 1996, now U.S. Pat. No. 6,015,913.

Reference is made to U.S. Pat. No. 5,554,645 (to Romanczyk et al.) issued Sep. 10, 1996, the disclosure of which is incorporated herein by reference.

FIELD OF THE INVENTION

The present invention relates to a versatile process for extracting fat from fat-containing beans and/or processing fat-containing beans to yield a solid product.

Documents are cited in this disclosure with a full citation for each appearing thereat. These documents relate to the state-of-the-art to which this invention pertains, and each document cited herein is hereby incorporated by reference.

BACKGROUND OF THE INVENTION

Cocoa beans are produced by cocoa trees which are found in warm, moist climates in areas about 20 degrees latitude north and south of the Equator. In general, the seeds of the *Theobroma cacao* (of the order Sterculiacae) are known chiefly in two varieties: Criollo and Forastero, with Forastero divided into several varieties. A third group, called Trinitario, is essentially a cross between Criollo and Forastero and is not found in the wild. Criollo beans are pale brown in color while Forastero beans are a purple hue. The cocoa tree produces leaves, flowers and fruit throughout the year, and the ripe fruit or pod resembles a long cantaloupe, typically containing from about 20 to 40 almond-shaped cocoa beans.

The cocoa bean is comprised of an inner nib portion covered by an outer shell. On a dry basis, the shell of the bean comprises about 12 to 15% of the weight of the bean, while the nib and residual moisture amounts to approximately 85 to 88%. Typical analytical data ranges for chemical components of cocoa nib are: fat content of 48 to 57%; theobromine content of 0.8 to 1.3%; caffeine content of 0.1 to 0.7%; total nitrogen content of 2.2 to 2.5%; ash content of 2.6 to 4.2%; and water content of 2.3 to 3.2% (see *Pearson's Composition and Analysis of Foods*, 9th Edition, 1991).

Various processes are traditionally employed to extract cocoa butter and cocoa solids from commercial cocoa beans. Typical methods of processing cocoa beans include the steps of (a) bean cleaning; (b) bean roasting; (c) bean winnowing; (d) nib grinding; (e) liquor pressing to produce cocoa butter and cocoa cake; (f) cake alkalizing; and (d) cake milling.

The initial step of typical cocoa bean processing methods consists of cleaning the beans to remove extraneous non-cocoa materials. Conventional bean cleaning separates beans from extraneous non-cocoa materials by either size or density using a cleaning machine which is a gravity, vibratory or aspiration table (See *Chocolate, Cocoa and Confectionery: Science and Technology*, 3rd Ed., by Bernard W. Minifie, page 35; *Chocolate Production and Use*, 3rd Ed., by L. Russell Cook, page 144–146; and *Industrial Chocolate Manufacture and Use*, 2nd Ed., by S. T. Beckett, page 55, hereby incorporated by reference).

Current cleaning technology is typically limited in separation ability to a minimum density difference of 10–15%. This reduces the efficiency of achieving an accurate separation of bean and extraneous non-cocoa materials and subsequently reduces the clean bean yield of the process. Additionally, conventional cleaning machines become easily clogged and require frequent cleaning. This also reduces the cleaning efficiency and the clean bean yield of the process.

Moreover, cleaning machines have a tendency to fracture the beans during cleaning which reduces the percentage of whole beans available after cleaning. These broken bean pieces can later give rise to problems during roasting and winnowing. For instance, small bean pieces will burn readily at the elevated temperatures used during roasting and may result in burnt and ashy flavored liquors which are unacceptable from a flavor viewpoint. Small bean pieces may also decrease the efficiency of the winnowing process because they can be lost during the aspiration of the shells and result in overall yield efficiency losses.

In most conventional processes, roasting of the whole bean or nib is an essential step in the manufacture of chocolate or cocoa. Roasting develops the natural flavor and aroma of the cocoa beans, and also loosens the shell so that it can be readily removed during the winnowing process. The degree of cocoa roast is a time/temperature dependent relationship, where the time can vary from 5 to 120 minutes and the temperature of the whole bean can typically vary from 125° C. to 150° C., and with respect to the roasting of nibs, an initial drying process step can be at just below 100° C. to remove the shell, with second stage roasting of nibs alone being at elevated temperatures up to about 130° C.; all of which depend on the construction of the machine, size of the batch and final product desired (See *Chocolate, Cocoa and Confectionery: Science and Technology*, 3rd Ed., by Bernard W. Minifie, incorporated herein by reference, especially page 37, 45–46; *Chocolate Production and Use*, 3rd Ed., by L. Russell Cook, page 146–152; and *Industrial Chocolate Manufacture and Use*, 2nd Ed., by S. T. Beckett, page 55–64, hereby incorporated by reference). U.S. Pat. No. 5,252,349 to Carter, Jr., hereby incorporated by reference, involves heating the bean to a temperature of about 152° C. to 160° C. for about 5 to 8 minutes.

The winnowing operation serves to separate the beans into the desired inner portion of the bean (nib) and the outer portion of the bean (shell). The principle of separation by a winnowing process depends on the difference in the apparent density of the nib and of the shell. Standard winnowing machines make use of the combined action of sieving and air aspiration. As discussed earlier, the shell is loosened during the conventional roasting step and/or other heating or drying steps. After loosening, the beans are typically broken between rollers or such devices to shatter the cocoa beans along natural fracture lines of the cocoa nib to facilitate shell removal during winnowing (see U.S. Pat. No. 2,417,078 to Jones, U.S. Pat. No. 5,252,349 to Carter, Jr., *Chocolate, Cocoa and Confectionery: Science and Technology*, 3rd Ed., by Bernard W. Minifie, page 47–51; *Chocolate Production and Use*, 3rd Ed., by L. Russell Cook, page 152–153; and *Industrial Chocolate Manufacture and Use*, 2nd Ed., by S. T. Beckett, page 67–68, hereby incorporated by reference).

Some cocoa bean processing techniques include the use of thermal pre-treatment equipment to aid in the separation of the shell from the nib. This involves giving the beans a thermal shock by hot air, steam or infra-red heat (see U.S. Pat. No. 4,322,444 to Zuilichem et al., and British Patent No. 1,379,116 to Newton, *Chocolate, Cocoa and Confectionery: Science and Technology*, 3rd Ed., by Bernard W. Minifie, page 44–43; *Chocolate Production and Use*, 3rd Ed., by L.

Russell Cook, page 155; and *Industrial Chocolate Manufacture and Use*, 2nd Ed., by S. T. Beckett, page 60–62, hereby incorporated by reference).

Infra-red pre-treatment uses infra-red heating to rapidly heat and expand the beans which assists in loosening the shells. The method consists of treating the beans with infra-red radiation for a period between one half and two minutes, during which time the beans are typically heated to a temperature of about 100 to 110° C. The infra-red radiation used has a wavelength between 2 and 6 microns which corresponds to a frequency in the range of 0.7 to $1.2 \times 10^8$ megacycles per second. This energy penetrates and excites the molecules of the bean which causes them to vibrate at their own frequency and results in rapid heating of the beans. However, there is no teaching or suggestion in the art of any processing technique involving heating, such as by infra-red, without a subsequent roasting.

The next step in most conventional cocoa processing, after winnowing, involves nib grinding. Nib grinding is typically performed in two stages, an initial grinding stage to convert the solid nibs into a fluid paste and a finish grinding stage to achieve the desired particle size. Both of these stages are asset, maintenance, and energy intensive.

The cleaned roasted cocoa nibs typically vary in cocoa butter content from 50–58% by weight. During the grinding, the nib is ground, for instance by milling, into a fluid, dark brown "liquor". The fluidity is due to the breakdown of the cell walls and the release of the cocoa butter during the processing. Ground particles of cocoa solids are suspended in the cocoa butter. This liquor is sometimes commercially sold as a product useful in the confectionery and baking industries where machinery for processing the cocoa beans is not available.

Most conventional cocoa processing includes separating cocoa butter from liquor. This is accomplished by using a batch hydraulic pot press ("hydraulic press") to separate the cocoa butter from the cocoa solids. The resultant cocoa butter is subsequently filtered to result in clear, solid-free cocoa butter. Butter can also be produced by utilizing a continuous screw press to extract the butter from whole bean with shell or less frequently, from nibs (see U.S. Pat. No. 5,252,349 to Carter, Jr.; and *Chocolate, Cocoa and Confectionery: Science and Technology*, 3rd Edition, by Bernard W. Minifie, hereby incorporated by references see especially pages 71–72 of Minifie).

The resulting cocoa cake from either hydraulic presses or screw presses may be milled into cocoa powder. Cocoa cake typically contains either 10–12% cocoa fat or 20–22% cocoa fat (See *Chocolate, Cocoa and Confectionery: Science and Technology*, 3rd Ed., by Bernard W. Minifie, page 72–76; *Chocolate Production and Use*, 3rd Ed., by L. Russell Cook, page 169–172; and *Industrial Chocolate Manufacture and Use*, 2nd Ed., by S. T. Beckett, page 78–82, hereby incorporated by reference). Cocoa powder from cocoa cake obtained by hydraulic pressing is usually produced by milling the cocoa cake. If natural cocoa powder is desired, cocoa cake is fed directly to the cocoa cake mill. If alkalized cocoa powder is desired, the cake from an alkalizing process is fed to the mill. Hydraulic pressing produces a cocoa cake which is an agglomerate of previously milled cocoa particles. Cocoa cake mills for cocoa cake from hydraulic pressing are therefore designed to reduce the size of these agglomerates. Conventional particle size reduction of cocoa cake from hydraulic pressing is typically performed by either hammer or disc mills in conjunction with particle size classification and separation. The classification and separation retains and returns particles larger than the size desired for further grinding. After milling, the powder is cooled and packaged.

The natural cocoa cake or natural cocoa powder can be further processed by alkalizing to improve the color and flavor qualities of the cake (see U.S. Pat. No. 3,997,680 to Chalin; U.S. Pat. No. 5,009,917 to Wiant, et al., *Chocolate, Cocoa and Confectionery: Science and Technology*, 3rd Ed., by Bernard W. Minifie, page 61–67; *Chocolate Production and Use*, 3rd Ed., by L. Russell Cook, page 162–165; and *Industrial Chocolate Manufacture and Use*, 2nd Ed., by S. T. Beckett, page 71–72, hereby incorporated by reference). The alkalizing process can be used at any of several different stages of processing and includes the treatment of either the beans, liquor, nib, cake or powder with solutions or suspensions of alkali, usually, but not limited to, sodium or potassium carbonate. After alkalizing, the cocoa solids are dried and cooled. The dried cocoa solids are subsequently milled to produce alkalized cocoa powder, and thereafter cooled and packaged.

U.S. Pat. No. 5,009,917 to Wiant et al., relates to a process to produce a deep red or black dutched cocoa by alkalizing cocoa presscake in a reaction vessel under pressure. The temperature of the process ranges from 150 to 300° F., the pressure ranges from 10 to 200 psi, and the time of the reaction ranges from 5 to 180 minutes. An oxygen containing gas is fed into the reaction vessel to maintain pressure and effect headspace changes at the rate of at least 3 per hour.

U.S. Pat. No. Nos. 4,871,562 and 4,7538,444 to Terauchi et al., hereby incorporated by reference, relate to a process for producing cocoa powder wherein either alkali treated cacao mass or cocoa powder is mixed with hot water; or cacao mass or cocoa powder is mixed with hot water containing an alkali; at 70° C. to 130° C. to dissolve the water-soluble portion in hot water. The water-soluble portion and fine particle portion mixture is isolated and dried to produce a cocoa powder.

U.S. Pat. No. 4,784,866 to Wissgott, hereby incorporated by reference, relates to improving the taste and dispersibility of cocoa by alkalizing the cocoa in an aqueous phase and heating in an enclosed vessel under pressure. The temperature of the process is below 110° C. and the pressure ranges from above one atmosphere to 3 atmospheres. An oxygen containing gas is fed into the vessel during at least a part of the mixing and heating for maintaining the excess pressure. After the cocoa is alkalized, water is evaporated from it.

U.S. Pat. No. 4,704,292 to Kattenberg, hereby incorporated by reference, relates to a method having the steps of moistening whole de-shelled cocoa beans (or a coarse fraction of cocoa nibs) with a hot concentrated alkaline processing liquid so that the processing liquid does not penetrate completely into the beans or nibs, followed by drying by means of infra-red radiation, roasting, coarse grinding, fine milling and pressing so as to remove cocoa butter and form a pressed cake, and pulverizing the pressed cake to form cocoa powder.

U.S. Pat. No. 3,923,847 to Roselius et al., hereby incorporated by reference, relates to a method that provides for the production of cocoa butter from cocoa mass or from unroasted or roasted crushed cocoa nibs by extraction with solvents wherein the cocoa product is subjected to extraction with a food-acceptable gas which is supercritical with respect to both pressure and temperature. The cocoa butter can thereafter be separated from the solution, e.g. by varying the pressure and/or temperature.

U.S. Pat. Nos. 3,955,489 and 3,904,777 to Goerling et al., hereby incorporated by reference, relate to a process for continuously producing roasted cocoa mass or liquor by removing the shells from the raw cocoa beans and crushing the de-shelled beans, if desired after a preceding drying and/or fracturing step, in order to produce a more or less thin, liquid cocoa mass and roasting the liquid cocoa mass under atmospheric or reduced pressure while moving the cocoa mass and heating it to a maximum temperature of about 150° C. through indirect heat transfer by means of a heating surface.

The vast majority of cocoa butter is conventionally derived from hydraulically pressing liquor obtained from fully roasted beans. It would be desirable to provide a method for producing both natural cocoa butter and natural and/or alkalized cocoa powders from cocoa nibs which is less labor, maintenance, energy and capital extensive than conventional methods.

Further, it has been recently found that cocoa beans contain substantial levels of polyphenols which have been extracted and screened for biological activity (see U.S. Pat. No. 5,554,645 to Romanczyk et al., incorporated herein by reference). Surprisingly, and contrary to the knowledge in the prior art, it has been discovered that cocoa polyphenol extracts which contain procyanidins have significant utility as anti-cancer or antineoplastic agents (see U.S. Pat. No. 5,554,645 to Romanczyk et al., incorporated herein by reference).

The extracts or compounds therefrom have generally been prepared, on a laboratory scale, by reducing cocoa beans to a powder, defatting the powder, and extracting and purifying the active compound(s) from the defatted powder (see U.S. Pat. No. 5,554,645 to Romanczyk et al.). The powder is generally prepared by freeze-drying the cocoa beans and pulp, depulping and dehulling the freeze-dried cocoa beans and grinding the dehulled beans (see U.S. Pat. No. 5,554,645 to Romancyzk et al.). The extraction of active compound(s) has been traditionally accomplished by solvent extraction techniques, and the extracts purified by gel permeation chromatography, preparative High Performance Liquid Chromatography (HPLC) techniques, or by a combination of such methods.

However, it has now been found that recovery of desired polyphenols appears to be inversely proportional to the times and temperatures used during cocoa bean processing, e.g., that which is required to achieve the desired roast of the cocoa beans; for instance, at or above 125° C. for about 5 to 120 minutes depending upon the equipment and raw materials used in the process). Therefore, cocoa butter or solids have not, heretofore, been produced having substantial quantities of desired polyphenols, due to the inherent limitations in the prior art methods of cocoa bean processing. And, these problems in the art have not heretofore been recognized.

Additionally, the methods outlined hereinabove, for isolating polyphenols from cocoa beans have been performed on a small scale. For instance, the scale may be said to be limited to analytical processing of the polyphenol samples obtained therefrom, because the isolation of polyphenols by those methods for later commercial use in products containing the active compounds may be said to be economically unfeasible. This problem, has not been heretofore recognized by the prior art.

Hence, it would be advantageous to provide a method for producing cocoa products having conserved levels of polyphenols relative to that found in the starting materials, in significant quantities, which can also be modified to an economical production of cocoa products which does not require separate roasting, liquor milling, and/or butter extraction equipment, such as hydraulic presses or solvent extraction equipment.

OBJECTS AND SUMMARY OF THE INVENTION

It is an object of the present invention to provide a method of processing a fat-containing bean, such as a cocoa bean, for producing solids having polyphenols and/or fat-containing products, comprising extracting the fat to produce solids and/or fat-containing products.

It is a further object of the present invention to provide a method of processing fat-containing beans, wherein the fat-containing bean further comprises an initial amount of at least one active polyphenol, and the solids derived from the inventive method further comprises a post-processing amount of the at least one active polyphenol, wherein the ratio of initial amount to post-processing amount is less than or equal to 2, preferably less than or equal to about 2.0 to 1.7 (e.g., about 1.8 or 1.9), more preferably less than or equal to about 1.4 to 1.6 (e.g., about 1.5), even more preferably about 1.1 to about 1.5 (e.g., about 1.3 or 1.4), and most preferably up to (and including) 1 (with 1.0=100% recovery; 1.1=91% recovery; 1.3=77% recovery; 1.5=67% recovery; 1.7=59% recovery; 1.9=53% recovery; 2.0=50% recovery).

It is an additional object of the invention to provide a method of processing fat-containing beans wherein the fat-containing bean further comprises at least one active polyphenol having the formula:

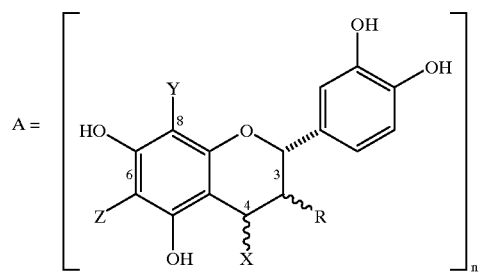

wherein:
n is an integer from 3 to 12, such that there is a first monomeric unit A, and a plurality of other monomeric units;
R is 3-(α)-OH, 3-(β)-OH, 3-(α)-O-sugar, or 3-(β)-O-sugar;
position 4 is alpha or beta stereochemistry;
X, Y and Z represent positions for bonding between monomeric units, with the provisos that as to the first monomeric unit, bonding of another monomeric unit thereto is at position 4 and Y=Z hydrogen, and, that when not for bonding monomeric units, X, Y and Z are hydrogen or Z, Y are sugar and X is hydrogen, or X is alpha or beta sugar and Z and Y are hydrogen, or combinations thereof; and
the sugar can be optionally substituted with a phenolic moiety via an ester bond.

Still further it is an object of the present invention to provide a method of processing fat-containing beans wherein the method further comprises the additional steps of bean selection, bean cleaning, removing the shell portion from the inner portion prior to extracting, and optionally, deodorization and alkalization.

Additionally, it is an object of the invention to provide cocoa solid compositions derived from a cocoa bean, wherein the cocoa solids have at least one active polyphenol of the formula:

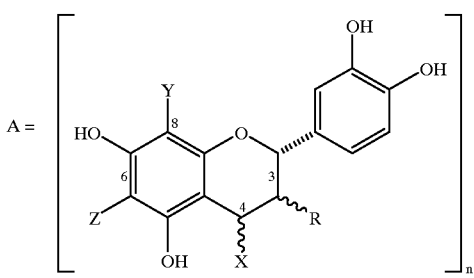

wherein:

n is an integer from 3 to 12, such that there is a first monomeric unit A, and a plurality of other monomeric units;

R is 3-(α)-OH, 3-(β)-OH, 3-(α)-O-sugar, or 3-(β)-O-sugar;

position 4 is alpha or beta stereochemistry;

X, Y and Z represent positions for bonding between monomeric units, with the provisos that as to the first monomeric unit, bonding of another monomeric unit thereto is at position 4 and Y=Z=hydrogen, and, that when not for bonding monomeric units, X, Y and Z are hydrogen or Z, Y are sugar and X is hydrogen, or X is alpha or beta sugar and Z and Y are hydrogen, or combinations thereof; and the sugar can be optionally substituted with a phenolic moiety via an ester bond.

Further, it is an object of the invention to provide a cocoa solid composition derived from a cocoa bean having at least one active polyphenol, wherein the concentration of the at least one active polyphenol with respect to the nonfat cocoa solids is conserved with respect to the concentration of the at least one active compound in the cocoa bean from which the solid is derived.

Additionally, it is an object of the present invention to provide a method of winnowing beans to remove the shell portion from the inner portion using an air fluidized bed density separation system.

These and other embodiments are disclosed or are obvious from the following detailed description.

BRIEF DESCRIPTION OP THE FIGURES

Figure 4A:
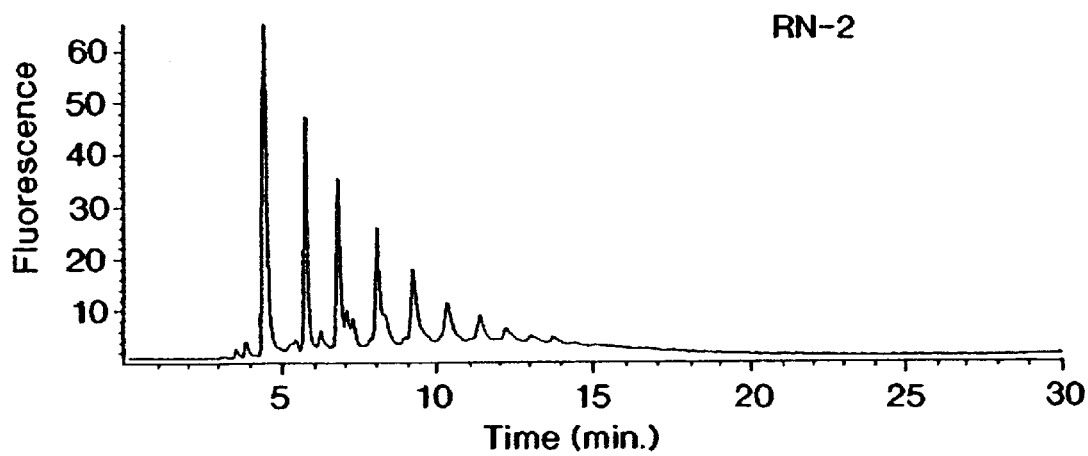
Figure 4B:
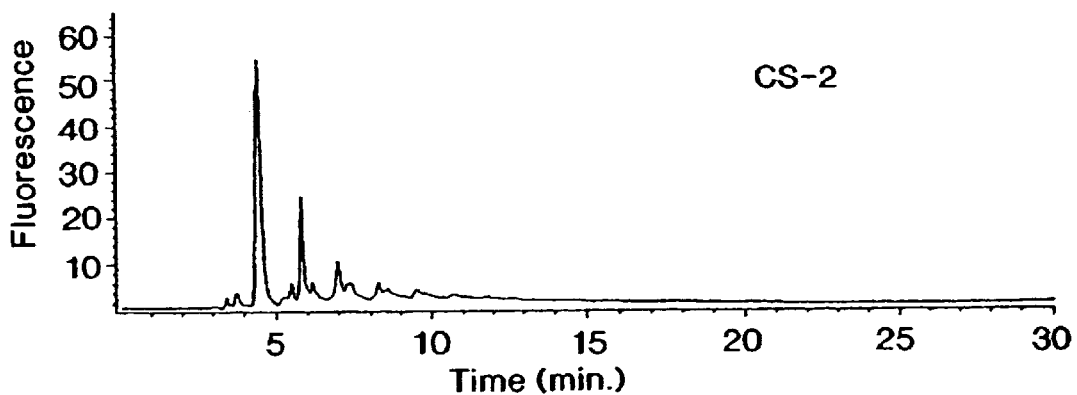

FIG. 4A shows a representative HPLC, normal phase chromatographic separation of cocoa polyphenols from sample RN-2, consisting of Sulawesi raw nibs, prior to processing by conventional methods; and FIG. 4B shows a representative HPLC, normal phase chromatographic separation of cocoa polyphenols from sample CS-2, consisting of cocoa solids, from Sulawesi raw beans (lot PTE2-5/06) after processing by conventional methods.

DETAILED DESCRIPTION OF THE INVENTION

The invention broadly relates to versatile methods of processing fat-containing beans, to extract the fat from the non-fat solids, and/or to obtain bean solids having conserved levels of polyphenols relative to the starting materials, and products derived therefrom.

Figure 1:
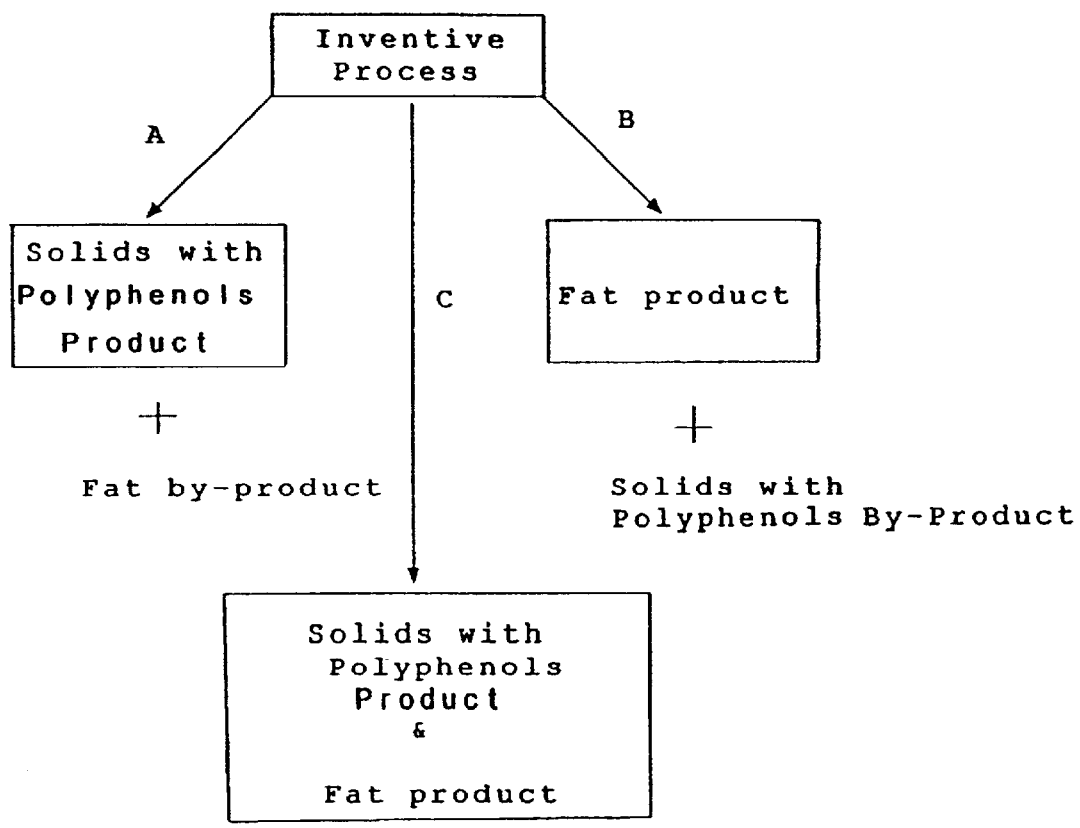
FIG. 1 shows an overview of the method of the present invention, and the various products which can be produced by the process (process options dependent upon economics of products, and/or by-products)

An outline of the process of the present invention is shown in FIG. 1. The method of the present invention enables the selective modification of certain steps of the process to produce three types of products. Modification A enables the production of solids containing conserved levels of active polyphenols relative to the starting material containing an initial concentration of polyphenols, such that the levels of polyphenols obtained are conserved beyond that which is seen in conventional processes. Modification B enables the production of fat products, omit, without necessarily the concomitant conservation of polyphenol actives. And, modification C enables the production of solids and fat products, with an enhanced conservation of polyphenol levels relative to that which is seen in conventional solid/fat separation processes.

Figure 2A:
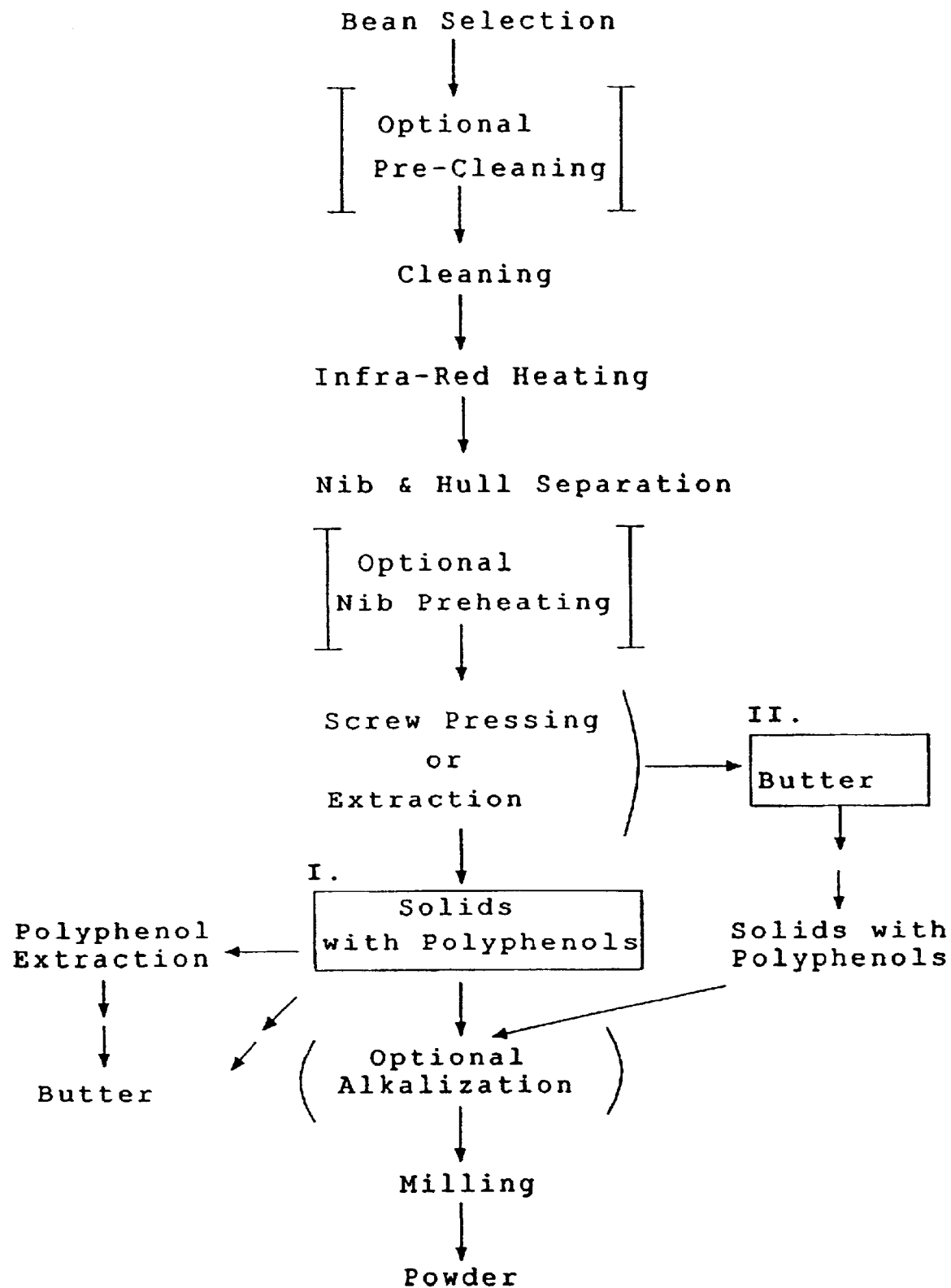
FIGS. 2A and 2B show overviews of the various steps of the method of the present invention using cocoa beans as an example.
Figure 2B:
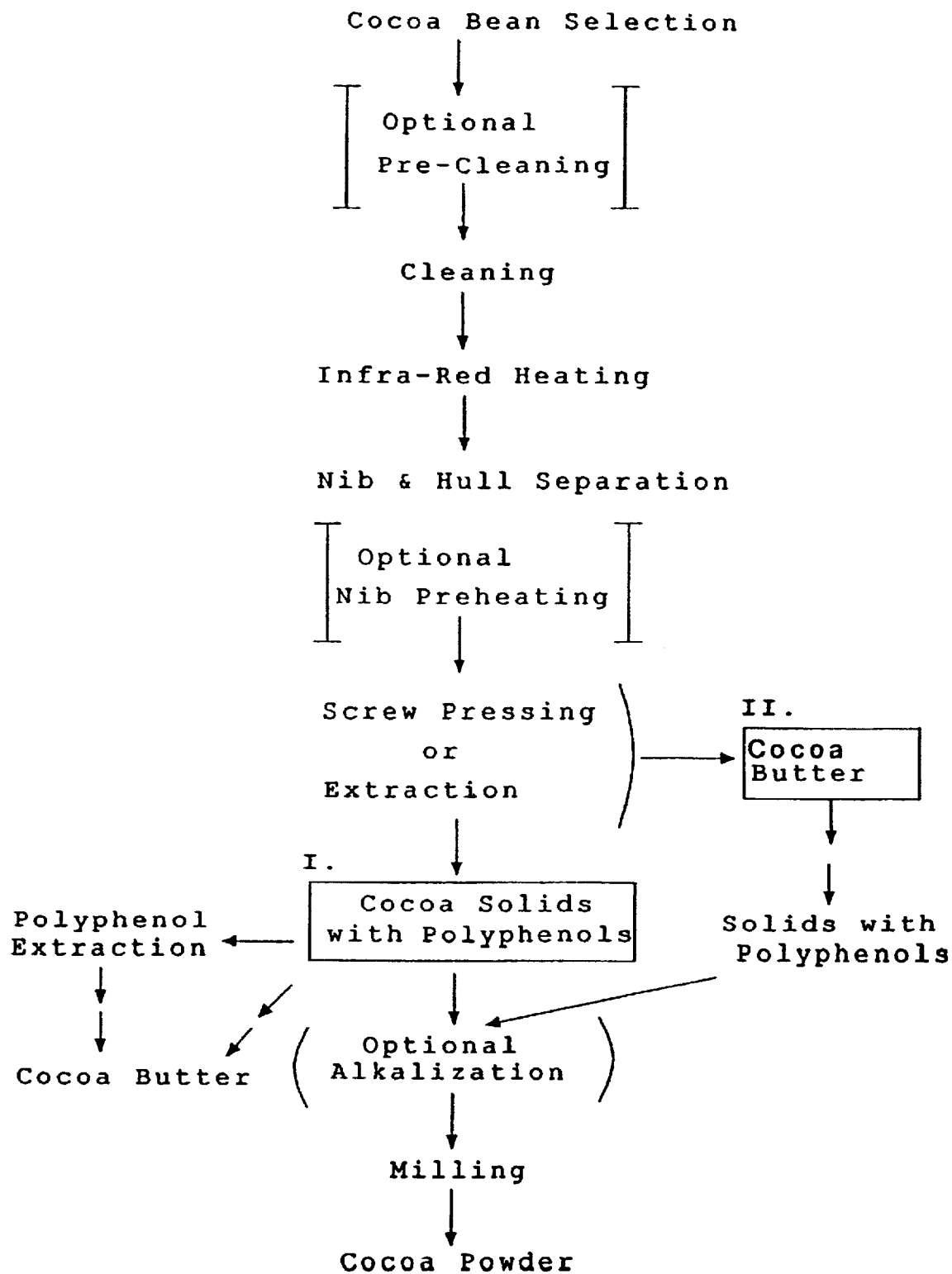
Figure 3A:
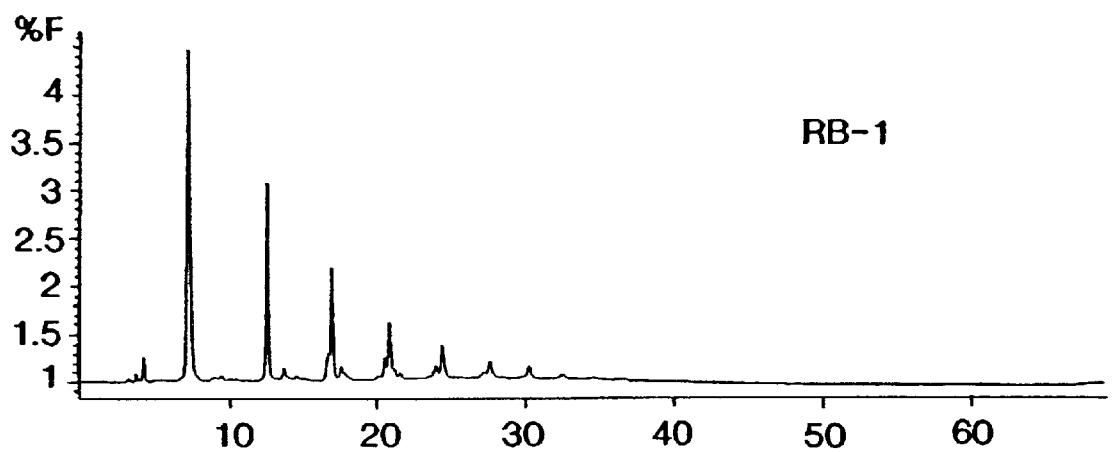
FIG. 3A shows a representative HPLC, normal phase chromatographic separation of cocoa polyphenols from sample RB-1 (lot PTE3-4/08), consisting of Sulawesi raw beans prior to processing by the method of the present invention.
Figure 3B:
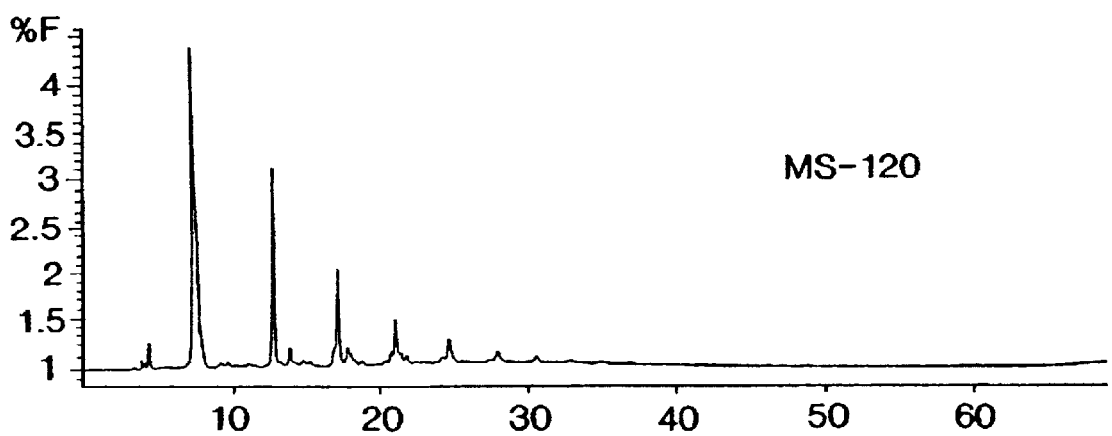
FIG. 3B shows a representative HPLC, normal phase chromatographic separation of MS-120, consisting of cocoa solids from Sulawesi raw beans processed according to the method of the present invention (at 120 psi; lot PTE3-4/08)

One aspect of the present invention relates to a process of extracting fat from fat-containing beans having an outer shell portion and an inner, nib portion, and/or to producing bean solids having conserved active polyphenols, comprising the steps outlined in FIGS. 2A and 2B. Box I represents product from modification A of FIG. 1; box II represents product from modification B; and both boxes I and II together represents products from modification C.

Fat-containing beans are appropriately selected according to the desired products of the process, and the beans are optionally subjected to a cleaning step to remove non-bean particulate matter. The beans are heated, preferably using infra-red radiation, sufficient to facilitate the separation of the nib from the hull. The nib can optionally be preheated, followed by fat extraction to produce fat products, i.e., butter, and bean solids having active polyphenols. The solids may be further processed by extraction to obtain the polyphenols, and/or to obtain refined solids and fat products. Additionally, the fat products obtained by fat extraction can be further processed to obtain solids having active polyphenols.

The methods of the present invention are applicable to any fat-containing bean having polyphenols, e.g., soy, sorghum or cocoa beans.

In a preferred embodiment, the bean is a cocoa bean and the fat is cocoa butter; and accordingly, analogous to FIG. 2A, FIG. 2B is an overview of the present invention with respect to that preferred embodiment. That is, the invention can be used to process beans from any species within the Theobroma or Herrania genera. Also, with reference to compositions containing polyphenols or isolation of polyphenols from cocoa, any species of Theobroma or Herrania, or their inter- and intra-species crosses thereof may be employed therefor, and reference in this regard is made to Schultes, "*Synopsis of Herrania*," Journal of the Arnold Arboretum, Vol. XXXIX, pp. 217 to 278, plus plates I to XVII (1958), Cuatrecasas, "Cacao and its Allies, A Taxonomic Revision of the Genus Theobroma," Bulletin of the United States National Museum, Vol. 35, part 6, pp. 379 to 613, plus plates 1 to 11 (Smithsonian Institution 1964), and Addison et al., "Observations on the Species of the Genus Theobroma Which Occurs in the Amazon," Bol. Tech. Inst. Agronomico de Nortes, 25, 3 (1951).

Further, cocoa beans comprising active polyphenols are disclosed in U.S. Pat. No. 5,554,685, wherein it is taught that cocoa beans containing active polyphenols have significant biological activity. See also, PCT/US95/12963, filed Oct. 3, 1995, and published Apr. 11, 1996 as WO 96/10404 and PCT/US96/04497, filed Apr. 2, 1996) and published Oct. 9, 1997 as WO 96/36597.

The pre-processed cocoa bean preferably comprises an initial amount of at least one active polyphenol, and the solids from processing (e.g., cake, powder), comprise a post-processing amount of the at least one active polyphenol. The present invention provides methods of processing beans such that the ratio of the initial amount of at least one active polyphenol to the post-processing amount of at least one active polyphenol is optimized. That is, the invention provides methods which conserve the amount of active polyphenol(s) remaining in the solids relative to that found in the starting material, i.e., the cocoa bean, and the method of the present invention can be utilized to enhance that amount.

Another aspect of the invention relates to a method of producing cocoa products wherein the ratio of initial amount to post-processing amount of active polyphenols is less than or equal to 2 preferably less than or equal to about 2.0 to 1.7 (e.g., about 1.8 or 1.9), more preferably less than or equal to about 1.4 to 1.6 (e.g., about.1.5), even more preferably about 1.1 to about 1.5 (e.g., about 1.3 or 1.4), and most preferably, up to (and including) 1 (with 1.0=100% recovery; 1.1=91% recovery; 1.3=77% recovery; 1.5=67% recovery; 1.7=59% recovery; 1.9=53% recovery; 2.0=50% recovery). The initial amount and post-processing amount may be determined, for example, by weight percentage with respect to the weight of non-fat cocoa solids. A 100% recovery of active polyphenols is ideal; and, of course, when desired, i.e., in this aspect of the invention approaching ideal as closely as possible, is most preferred.

As set forth above, the beans may contain at least one active polyphenol. Preferably, the at least one active polyphenol includes at least one active compound of the formula:

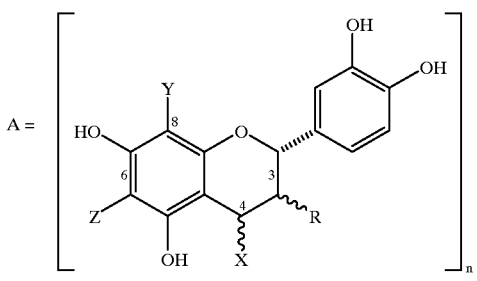

wherein:
  n is an integer from 3 to 12, such that there is a first monomeric unit A, and a plurality of other monomeric units;
  R is 3-(α)-OH, 3-(β)-OH, 3-(α)-O-sugar, or 3-(β)-O-sugar;
  position 4 is alpha or beta stereochemistry;
  X, Y and Z represent positions for bonding between monomeric units, with the provisos that as to the first monomeric unit, bonding of another monomeric unit thereto is at position 4 and Y=Z hydrogen, and, that when not for bonding monomeric units, X, Y and Z are hydrogen or Z, Y are sugar and X is hydrogen, or X is alpha or beta sugar and Z and Y are hydrogen, or combinations thereof; and
  the sugar can be optionally substituted with a phenolic moiety via an ester bond.

One embodiment of the invention is directed to a cocoa solid wherein the concentration of the total procyanidin to nonfat cocoa solids is greater than 20,000 ug/g, preferably greater than 25,00 ug/g, more preferably, greater than 28,000 ug/g, and most preferably greater than 30,000 ug/g.

Advantageously, the at least one active procyanidin comprises a pentamer wherein n is 5, and the concentration of the pentamer to the nonfat cocoa solid is greater than 1000 ug/g, or, more preferably, the concentration is greater than 1500 ug/g.

Accordingly, the methods of the present invention further comprise the step of isolating the at least one active procyanidin from solids, such as the de-shelled nib.

The inventive process can be modified to optimize the desired products. According to a further embodiment of the invention, the modifications which can be made to the process are outlined in Table 1. Modifications A (for obtaining solids having conserved levels of active procyanidins as product, with butter as by-product), B (for obtaining cocoa butter as product with solids as by-product) and C (for obtaining both solids having active polyphenols and butter as products) are separated in Table 1 according to each of the steps of the process (the order of steps listed in Table 1 is necessarily suggested of a preferred order; the order of the steps may be as set forth or may be varied).

According to the present invention bean selection now enables one skilled in the art to select types of cocoa beans which are optimal for the desired products. Beans may be selected according to species and level of fermentation, as evidenced by the color of the beans.

TABLE 1

MODIFICATIONS OF THE INVENTIVE PROCESS

| Steps in Inventive Process | A (Solids) | B (Butter) | C (Solids/Butter) |
|---|---|---|---|
| BEAN SELECTION | Slaty and/or purple | brown-slaty (inclusive); preferably brown | purple/brown |
| CLEANING | optional, but preferred | preferred | preferred |
| MICRONIZING (Heating) | optional, temps ≦105° C. | optional; but preferred 110–165° C. (125–135° C. preferred) | 95–135° C. (100–105° C. preferred) |
| ROASTING | HTST optional | optional | HTST optional |
| WINNOWING | optional, but preferred especially with fluidized bed | optional, but preferred especially with fluidized bed | preferred especially with fluidized bed |
| MILLING | (cold milling optional) | — | (cold milling optional) |
| SCREW PROCESSING | preferred | preferred | preferred |
| SOL- | preferred for | optional | optional |

TABLE 1-continued

MODIFICATIONS OF THE INVENTIVE PROCESS

| Steps in Inventive Process | A (Solids) | B (Butter) | C (Solids/Butter) |
|---|---|---|---|
| VENT EXTRACTION | polyphenol isolation | | |
| DEODORIZATION | — | may be required for butter if solvent extracted | may be required for butter if solvent extracted |
| ALKALIZATION | may be optional after extraction of polyphenols | may be optional after extraction of polyphenols | may be optional after extraction of polyphenols) |
| VALUE OF SOLIDS (quality, e.g., recovery of polyphenols and quantity) | at least 70%; nearly 100% conserved polyphenols (preferably at least 85% to nearly 100%) | 50–70% preferably at least 70% conserved polyphenols | at least 70%, preferably, 70 to 95% or more conserved polyphenols; preferably food grade |
| VALUE OF BUTTER (quantity and purity) | moderate | highest (preferably food grade) | moderate to highest; preferably food grade |

1. Micronizing temperatures are internal bean temperatures (defined below).
2. HTST refers to High Temperature Short Time (defined below).

In order to assess the degree of fermentation, the beans are subjected to a cut test, which is the standard method of assessing quality as defined in grade standards. A cut test involves cutting lengthwise approximately 300 beans taken from a random sample of the cocoa whose level of fermentation is to be assessed. The bean halves are laid out on a board for visual inspection of the color, as well as the defects which can occur during bean growth and harvesting. Defects in cocoa beans include: mould, insect damage, germination; wherein the shell of the bean has been pierced, slit or broken by the growth of the seed germ; and the presence of a flat bean, in which the cotyledons are too thin to be cut to give a surface of cotyledon.

The beans can be divided into four categories, according to their color: fully fermented, i.e., predominantly a brown hue; purple/brown; purple; and slaty, wherein slaty beans represent unfermented beans. Purple/brown beans include all beans showing any blue, purple or violet color on the exposed surface, whether suffused or as a patch. Purple beans should include all beans showing a completely blue, purple or violet color over the whole exposed surface. This should also include, irrespective of color, any beans which are slaty, but not predominantly so (wherein predominantly, in this context, means more than half).

The colors of a normal sample of cut beans cover a range from the brown of fully fermented beans to the fully purple of beans that have been inadequately fermented. Inadequate fermentation of a sample of beans is evidenced by greater than or equal to 50% of the beans being slaty in color. While the definitions of the aforementioned categories are a general guide, the assessment according to these categories is well within the scope of knowledge of the ordinary skilled artisan well versed in chocolate and cocoa processing (see *Cocoa, Fourth Ed.*, by Wood et al., 1985, incorporated herein by reference, especially pages 511 to 513).

As shown in Table 1, beans which are preferable for use in modification A can be slaty and/or purple. Beans which are preferable for use in modification B contain brown to slaty beans; and beans which are preferable for use in modification C are purple/brown in color. In the processing of cocoa beans to food products such as cocoa and chocolate, slaty beans are not desired; thus, another advantage of the present invention is a use for cocoa beans not heretofore considered desirable.

In a preferred embodiment, unfermented beans, i.e., slaty beans, are used in modification A to yield cocoa solids having highly conserved levels of active polyphenols.

In another embodiment of the invention, beans are optionally cleaned using an air fluidized bed density separator (AFBDS) prior to heating (micronizing). The cocoa beans may also be subjected to a pre-cleaning step prior to cleaning in the AFBDS. Heretofore, bean cleaning was performed by gravity, vibratory or aspiration tables, not by an. AFBDS and, prior to the present invention, the use of an AFBDS for cleaning has not been taught or suggested.

In a preferred embodiment, modification A optionally employs a cleaning step to obtain cocoa solids for conservation of active polyphenols. Preferably, the use of an AFBDS in the cleaning step is employed in modification A. Further, modifications B and C utilize a cleaning step to obtain cocoa butter and/or cocoa solids and butter containing active polyphenols.

Micronizing (heating e.g., infra-red heating) is employed to reduce the moisture content of the cocoa beans to approximately 3% by weight. The heating step is preferably done by infra-red heating, for a time ranging from about 3 to about 4 minutes, in order to minimize loss of moisture and conserve active polyphenols.

In Table 1, in the row labeled micronizing, the temperatures provided are internal bean temperatures ("IBT"); and, these temperatures are different from temperatures discussed in the Background of the Invention with respect to roasting (the temperatures discussed in the Background of the Invention with respect to roasting are equipment operational temperatures).

The internal bean temperature (IBT) can be measured by filling an insulated container such as a thermos bottle with beans (approximately 80–100 beans). In order to maintain the temperature of the beans during transfer from the heating apparatus to the thermos, the insulated container is then appropriately sealed in order to maintain the temperature of the sample therein. A thermometer is inserted into the bean filled insulated container and the temperature of the thermometer is equilibrated with respect to the beans in the thermos. The temperature reading is the IBT temperature of the beans. IBT can also be considered the equilibrium mass temperature of the beans.

According to one embodiment, modification A optionally employs a heating step, as sustained high temperatures are detrimental to polyphenols in the cocoa beans. Preferably, the heating step is performed at a minimal operating temperature and time to loosen the shell, and the beans are immediately cooled to ambient temperature. More preferably, micronization (heating) is performed at a temperature less than or equal to 105° C. IBT for modification A of the present invention.

According to a further embodiment of the invention, the cocoa butter extraction of modification B is optimized by heating to an equilibrium mass temperature of between 110 to 165° C. IBT, and more preferably, at a temperature between 125 and 135° C. IBT.

Additionally, modification C may employ a heating step at a temperature of between 95 and 135° C. IBT, and more preferably, a temperature of between 100 to 105° C. IBT, or a minimal temperature sufficient to remove the shell. The bean is not heated to a temperature above the outer limits of the preferred ranges for a period of time greater than 5 minutes, to optimize both fat extraction and yield of active polyphenols.

The lower temperature and short time heating method allows for an enhanced yield of active polyphenols.

According to a preferred embodiment of the invention, the methods are performed without the use of a roasting step. However, as an alternative to roasting, a high temperature, short time (HTST) process may be used in modifications A and C, in order to remove shell and give a roasted flavor note to the products of A and C, which additionally contain active polyphenols in the solids. In a preferred embodiment, a HTST process employs operational temperatures greater than 170° C. for less than 3 minutes. Preferably, the operational temperature of the HTST process is greater than 170° C. for less than 2 minutes; more preferably, the temperature is greater than 180° C. for less than 1 minute; and most preferably, the operational temperature is greater than 190° C. for less than 30 seconds.

In a further embodiment of the present invention, beans may be subjected to a winnowing step to separate the shell from cocoa nibs prior to the pressing step.

The cocoa shells of the cocoa bean are removed from the beans to produce nibs. Conventional winnowing includes cracking the beans along their natural fracture lines to produce a mixture of nibs and shells, followed by sieving of the mixture by size and air aspiration for separation of the shells from the nibs. Suitable conventional apparatuses include those made by Barth, Buhler, Lehmann, Bauermeister and others. Such apparatuses are more effective when used according to the present invention since the fee into the winnowing device is comprised of a higher percentage of cleaner, whole beans from the AFBDS. The cleaner, whole beans entering the cracking stage of the winnower produces fewer small pieces of nib or nib fines than achievable from conventional cleaning equipment. Nib fines are difficult for air aspiration to differentiate and separate from shells because of their similarity in weight and/or density. This results in a large percentage of the nib fines being removed with the shells. Loss of usable nibs from the present invention is reduced to less than 4% of the shell stream as compared to 4–8% for conventional processes.

Advantageously, winnowing is performed using an AFBDS. Accordingly, an AFBDS may be used to clean the beans and also during the winnowing, e.g., in sequence. The advantage of simplifying apparatus employed in the processing of beans, i.e., the use of an single type of apparatus for cleaning and winnowing is that it reduces the number of types of apparatus necessitated by the process which simplifies maintenance and repair issues. These advantages have not heretofore been suggested or taught in the prior art.

Using an air fluidized-bed density separator as a winnower surprisingly meets the FDA requirements for the maximum amount of shell in the nib product (below 1.75%), and results in less than 2% nib in the shell by-product. Suitable units include those manufactured by Camas or, more specifically, the apparatus set forth in U.S. Pat. No. 5,244,099 to Zaltzman et al., hereby incorporated by reference.

Conventional winnowing apparatuses such as those manufactured by Barth, Buhler, Lehmann, Bauermeister and others typically operate at an efficiency of around 1% shell remaining in nib and 4–8% nib remaining in the shell. The amount of shell remaining in the nibs is typically measured by handpicking the shell from a sample of nibs from the winnower and calculating the percentage of shell by weight in the nibs. The nib in shell content is typically determined by measuring the level of fat in the shell stream and converting this measurement into a nib content which assumes a fat content of the nibs at 50%.

According to the present invention, the beans are cracked along their natural fracture lines to produce a mixture of nibs and shells. The cracked beans are then fed into the AFBDS and the denser nibs are separated from the lighter shells by the fluidizing air. The AFBDS is composed of four separating chambers which allow for increasingly precise control of the density separation. To provide sizing capabilities to the AFBDS, vibrating screens such as those manufactured by Sweco may be used to regulate the size of the nibs and the shells to further enhance the density separation between the chambers. The use of an AFBDS in conjunction with sizing screens produced a shell in nib level of less than 0.2% and a nib in shell level of less than 2.0%. This provides a much cleaner nib product with much less waste as compared to conventional processes.

In a preferred embodiment, modifications A and B employ winnowing, preferably the AFBDS, although winnowing is optional in both modifications. In modification A, winnowing is preferred, as it leads to a high concentration of the actives in the cocoa solids. In modification B, winnowing is optional, although, preferred, as shells can harbor trapped microorganisms which may be eliminated by winnowing. Modification C preferably employs winnowing, preferably the AFBDS. Preferably, the cocoa solids are substantially free of bean shell material.

Milling, used in conventional processes to maximize the surface area of the beans for subsequent fat extraction, is optional in the method of the present invention, although milling may be detrimental, as it constitutes an oxidative and thermal abuse to the active polyphenols. Cold-milling or trituration, wherein a fluid, for instance a cooling fluid, such as liquid nitrogen is employed, may optionally be employed in modification A, where conservation of polyphenol actives is desirable.

The fat is preferably extracted without the use of a liquor grinding step. The extraction step may include, for example, screw pressing, whereby cocoa butter is extracted and cocoa solids having conserved levels of the at least one active polyphenol is obtained.

According to a further embodiment of the invention, cocoa beans, with or without shells, are screw pressed to form cocoa butter and cocoa cake containing enhanced levels of active polyphenols.

According to another embodiment, fat can be extracted from cocoa beans by known methods of oil extraction from oil seeds. The extraction of fat can be accomplished by low temperature or high temperature (or steam) processes wherein fat is extracted in the presence of water, under high temperature and pressure, in a closed vessel. Further, digestive processes can be employed, wherein the wet separation of fats is facilitated by the addition of chemicals or enzymes which promote separation of fat by hydrolysis and dissolution.

Additionally, batch pressing can be employed in the method of the present invention, wherein fat extraction comprises the application of pressure to batches of the cocoa beans confined in bags, cloths, cages or other suitable devices. It must be appreciated that the aforementioned processes of fat extraction can be modified appropriately by the skilled artisan without the burden of undue experimentation to optimize the levels of active cocoa polyphenols in the products derived therefrom, such that the skilled artisan would recognize that modifications in the aforementioned processes, i.e., temperature, pressure, and the addition of chemicals or enzymes which promote the dissolution of fat may be appropriately adjusted according to the sensitivity of active polyphenols to extremes in temperature, pressure and chemical and/or enzymatic degradation.

Further, solvent extraction of fat from cocoa beans is applicable to the method of the present invention, using light paraffinic petroleum fractions, hydrocarbon, alcohol, supercritical-fluid, and other polar and non-polar solvents, or mixtures thereof (see *Bailey's Industrial Oil and Fat Products*, 4th Ed., Vol. 2, Daniel Swern (Editors), 1982, incorporated herein by reference, especially pp. 175 to 251).

In a preferred embodiment of the present invention, screw pressing is utilized in modifications A, B and C.

In an additional embodiment of the present invention, solvent extraction is preferably employed in modification A for isolation of cocoa polyphenols from the solids. If the resultant cocoa solids after removal are for consumption, subsequent processing should be employed to reduce solvent residue to acceptable levels. (e.g. FDA, USDA, and Good Manufacturing Practices requirements); and the solids may also be deodorized and may optionally be alkalized. Solvent extraction may optionally be employed in modifications B and C for isolation of polyphenols and/or to maximize butter yield, but with the added expense of further processing of the butter and solids to reduce solvent residue to acceptable levels (if a consumable final product is desired) and by deodorization and alkalization. However, deodorization and alkalization processes are detrimental to the active cocoa polyphenols, and should be reserved for production of consumable products without conserved levels of cocoa polyphenols.

In Table 1, Value of Solids is relative to quality of the solids, e.g., recovery of cocoa polyphenols, and quantity of solids obtained (although parameters for consumable solids may also be considered). Value of Butter is relative to quantity obtained and purity. Highly pure butter is substantially free of non-cocoa butter fats, solids, and free fatty acids (less than 2.0% measured as oleic) as well as shell, and has low levels of microbial contamination (not to exceed 1,000 counts per gram, total plate count).

A further aspect of the invention relates to products containing the fat or solids obtained from the inventive processes, such as compositions comprising conserved levels of active cocoa polyphenols, or cocoa solids, such as cake or powder comprising conserved levels of active cocoa polyphenols, either alone or optionally with a suitable carrier or diluent for the cocoa polyphenols. Such products include edible compositions such as foods containing the cocoa compositions produced by the inventive methods. Preferably, these include chocolates or chocolate-flavored foods, confections or drinks (fluids) containing the cocoa products, particularly the cocoa products with high yields of cocoa polyphenols.

Sweet chocolate differs from milk chocolate in that it requires more chocolate liquor and limits the amount of milk solids. Semisweet chocolate requires at least 35% by weight chocolate liquor and is otherwise similar in definition to sweet chocolate. Commonly known dark chocolate, generally containing only chocolate liquor, a nutritive carbohydrate sweetener and cocoa butter, is by definition either a sweet chocolate or a semisweet chocolate. Buttermilk chocolate and skim milk chocolate differ from milk chocolate in that the milk fat comes from various forms of sweet cream buttermilk and skim milk, respectively, and in the case of skim milk, the total amount of milkfat is limited to less than the minimum for milk chocolate.

Mixed dairy product chocolates differ from milk chocolate in that the milk solid includes any or all of the milk solids listed for milk chocolate, buttermilk chocolate or skim milk chocolate. White chocolate differs from milk chocolate in that it contains-no non-fat cocoa solids. As used herein, the term "chocolate" denotes chocolate, baking chocolate, milk chocolate, sweet chocolate, semisweet chocolate, buttermilk chocolate, skim milk chocolate, mixed dairy product chocolate, white chocolate and non-standardized chocolates, unless specifically identified otherwise.

Chocolate used in food in the United States is subject to a Standard of Identity established by the U.S. Food and Drug Administration (FDA) under the Federal Food, Drug and Cosmetic Act. The U.S. definitions and standards for the various types of chocolate are well established. Nonstandardized chocolates are those chocolates which have compositions which fall outside the specified ranges of the standardized chocolates.

Examples of nonstandardized chocolates result when the cocoa butter or milkfat are replaced partially or completely; or when the nutritive carbohydrate sweetener is replaced partially or completely; or flavors imitating milk, butter or chocolate are added or other additions or deletions in formula are made outside the U.S. FDA Standards of Identify for chocolate or combinations thereof.

As a confection, chocolate can take the form of solid pieces of chocolate, such as bars or novelty shapes, and can also be incorporated as a component of other, more complex confections where chocolate is combined with and generally coats other foods such as caramel, nougat, fruit pieces, nuts, wafers or the like. These foods are characterized as microbiologically shelf-stable at 65–85° F. under normal atmospheric conditions. Other complex confections result from surrounding with chocolate soft inclusions such as cordial cherries or peanut butter. Other complex confections result from coating ice cream or other frozen or refrigerated desserts with chocolate. Generally chocolate used to coat or surround foods must be more fluid than chocolates used for plain chocolate solid bars or novelty shapes.

Additionally, chocolate can also be a lowfat chocolate comprising a fat and nonfat solids, having nutritive carbohydrate sweetener(s), and an edible emulsifier. As to lowfat chocolate, reference is made to U.S. Pat. Nos. 4,810,516, 4,701,337, 5,464,649, 5,474,795 and WO 96/19923.

Compositions of the invention comprising the active cocoa polyphenols such as obtained by the inventive methods can be formulated into compositions, for instance edible compositions, such as chocolate, as therapeutic or dietary compositions. Such compositions, or isolated active cocoa polyphenols can be administered to a subject or patient in need of such therapeutics or dietary supplement in dosages and by techniques well known to those skilled in the medical, nutritional or veterinary arts, taking into consideration such factors as the age, sex, weight and condition of the particular subject or patient. The compositions can be administered alone, or in suitable admixture with other antineoplastic, anti-tumor or anti-cancer agents, antioxidants, DNA topoisomerase II enzyme inhibiting agents, or cyclo-oxygenase and/or lipoxygenase, blood or in vivo glucose or NO or NO-synthase modulating agents and/or with agents which reduce or alleviate ill effects of antineoplastic, anti-tumor, anti-cancer, antioxidants, DNA topoisomerase II enzyme inhibiting agents, cyclo-oxygenase and/or lipoxygenase modulators, blood or in vivo glucose or NO or NO-synthase modulating agents; again, taking into consideration such factors as the age, sex, weight, and condition of the particular subject or patient.

The following non-limiting Examples are given by way of illustration only and are not to be considered a limitation of this invention, many apparent variations of which are possible without departing from the spirit or scope thereof.

EXAMPLES

Example 1

Method of Obtaining Cocoa Butter from Cocoa Beans Utilizing the Inventive Process Commercially available cocoa beans having an initial moisture content of from about 7 to 8 percent by weight were pre-cleaned using an 11"×56" Scalperator (manufactured by Carter Day International, Minneapolis, Minn., USA). Approximately 600 bags of cocoa beans (39,000 kg) were pre-cleaned over a 6.5 hour time period. The beans were fed into the inlet hopper where the flow rate was regulated by a positive feed roll. The beans were fed onto the outside of a rotating wire mesh scalping reel. The beans passed through the wire mesh reel and subsequently through an air aspiration chamber where light dirt, dust and strings were aspirated out of the product stream. The beans that did not pass through the scalping reel were conveyed to the reject stream. This reject stream consisted of large clumps of beans, sticks, stones, etc. The amount of resultant reject was approximately 150 kg, or 0.38% of the starting material. The resulting pre-cleaned product weighed about 38,850 kg and was passed to the bean cleaning step.

The pre-cleaned bean products from the Scalperator were then further cleaned using a Camas International SV4–5 Air Fluidized Bed Density Separator (AFBDS, manufactured by Camas International, Pocotello, Id., USA). About 38,850 kg of cocoa bean products were fed into the ADBDS over a time period of about 6.5 hours. The apparatus removed substantially all heavy impurities such as stones, metal, glass, etc. from the beans, as well as lighter unusable materials such as moldy and infested cocoa beans, resulting in a cleaned bean product which contained substantially only usable cocoa beans. The resulting heavy impurities removed weighed about 50 kg and the light unusable materials weighed about 151 kg. A total of about 38,649 kg of cleaned beans was obtained after both the pre-cleaning and cleaning steps described hereinabove (99.1% yield after cleaning).

The cleaned cocoa beans were then passed through a infra-red heating apparatus. The apparatus used was the Micro Red 20 electric infra-red vibratory Micronizer (manufactured by Micronizing Company (U.K.) Limited, U.K.). The Micronizer was run at a rate of about 1,701 kilograms per hour. The depth of beans in the vibrating bed of the Micronizer was about 2 inches or about 2–3 beans deep. The surface temperature of the Micronizer was set at about 165° C., resulting in an IBT of about 135° C., for a time ranging from 1 to 1.5 minutes. This treatment caused the shells to dry rapidly and separate from the cocoa nib. Since substantially all of the cocoa beans fed into the Micronizer were whole beans and were substantially free of small broken pieces of bean or shell, no sparks or fires were observed during the Micronizing step. The broken pieces separated by the vibrating screen prior to the Micronizer were re-introduced into the product stream prior to the winnowing step.

The beans after the Micronizer had a moisture content of about 3.9% by weight. The beans emerged from the Micronizer at an IBT of about 135° C. and were immediately cooled to a temperature of about 90° C. in about three minutes to minimize additional moisture loss. The total beans available after the heating step was about 36,137 kg.

The beans were then subjected to winnowing using a Jupiter Mitra Seita winnower (manufactured by Jupiter Mitra Seita, Jakarta, Indonesia). The winnowing step cracked the beans to loosen the shells and separated the lighter shells from the nibs while at the same time minimizing the amount of nib lost with the shell reject stream. The feed rate into the winnower was about 1,591 kg per hour. The resultant products included about 31,861 kg of usable nibs and 4,276 kg of reject shells. The overall yield of usable nibs from starting material was about 81.7%.

The resulting cocoa nibs were pressed using a Dupps 10–6 Pressor (manufactured by The Dupps Company, Germantown, Ohio, USA). A steady, consistent feed of about 1,402 kg per hour of nibs was fed into two screw presses to extract butter. The press produced about 16,198 kg of cocoa butter which-contained about 10% cocoa solids, and about 15,663 kg of cocoa solids which contained about 10% butter.

The cocoa butter was further processed using a Sharples P3000 decanting centrifuge (manufactured by Jenkins Centrifuge Rebuilders, N. Kansas City, Mo., USA). The centrifugation resulted in the removal of the solids from the butter by centrifugal forces. The centrifuging reduced the 10% solids in the butter to about 1–2% solids, and resulted in about 13,606 kg of butter and 2,592 kg of cocoa solids containing about 40 to 45% butter.

The butter containing 1–2% solids was further processed using a plate and frame filter (manufactured by Jupiter Mitra Seita) which removed the remaining solids from the butter and resulted in about 13,271 kg of clear cocoa butter and about 335 kg of cocoa solids containing 40–45% butter.

The cocoa solids removed from the centrifuge and the filter press contained about 40–45% fat and were pressed in a batch hydraulic press to produce 10% fat cocoa cake. This material produced about 1,186 kg of clear butter and 1,742 kg of cocoa solids.

The total clear butter yield from the incoming beans was 14,456 kg, or 37.1%. The total cocoa solids produced from the incoming beans was 17,405 kg, or 44.6%. The butter was subsequently tempered and packaged.

Example 2

Method for Quantitating Cocoa Procyanidin Levels in Various Samples Processed by Conventional and Inventive Methods A set of cocoa samples, listed in Table 2, (6–7 g) were ground to a fine powder using a Tekmar A-10 Analytical Mill for 5 minutes. The samples were transferred to a 50 ml polypropylene centrifuge tube, and approximately 35 ml of hexane was added, and the samples were shaken vigorously for 1 minute. The samples were centrifuged at 3000 rpm for 10 minutes using an International Equipment Co. IECPR-7000 Centrifuge, and the hexane layer was decanted. This fat extraction procedure was repeated for a total of three extractions. Approximately 1 g of the resultant defatted material was weighed into a 50 ml polypropylene centrifuge tube, and 5 ml of. a solution containing 70% acetone: 29.5% water: 0.5% acetic acid solution was added. The sample was vortexed for approximately 30 seconds using a Scientific Industries Vortex Genie 2, and spun at 3000 rpm for 10 minutes in the IEC PR-7000 Centrifuge. The supernatant was filtered into a 1 ml hypovial through a Millex-HV (Millipore) 0.45um filter.

Cocoa procyanidin extracts were analyzed by a Hewlett Packard 1090 Series II HPLC system equipped with a HP Model 1046A Programmable Fluorescence detector and Diode Array detector. Separations were effected at 37° C. on a 5 um Supelco Supelcosil LC-Si column (250×4.6 mm) connected to a Supelco Supelguard LC-Si 5 um guard column (20×2.1 mm). Procyanidins were eluted by a linear gradient under the following conditions: (time, %A, %B, %C); (0, 76, 20, 4); (25, 46, 50, 4); (30, 10, 86, 4); followed by a 5 minute re-equilibration. The mobile phase composition was A=dichloromethane, B=methanol, and C=acetic acid:water at a volume ratio of 1:1. A flow rate of 1 ml/min was used. Components were detected by fluorescence, where $\lambda_{ex}$=276 nm and $\lambda_{em}$=316 nm or by UV at 280 nm. Epicatechin was used as an external standard. Representative HPLC chromatograms showing the separation of procyanidins from samples, RB-1, MS-120, RN-2 and CS-2 are shown in FIGS. 3A, 3B, 4A and 4B.

TABLE 2

Polyphenol Content
Defatted Dry Weight Basis

| Sample | Description | Oligomer Amount (μg/g) | | | | | | | | | Total Polyphenol |
|---|---|---|---|---|---|---|---|---|---|---|---|
| | | Monomer | Dimer | Trimer | Tetramer | Pentamer | Hexamer | Heptamer | Octamer | Nonamer | |
| 937-59 | Inventive (Sulawesi unfermented screw pressed cocoa) | 9433 | 5929 | 5356 | 4027 | 3168 | 2131 | 1304 | 739 | 439 | 32743 |
| E1 | Comparative (screw pressed cocoa cake-Sulawesi) | 8713 | 5538 | 3880 | 2289 | 1553 | 762 | 372 | 210 | 60 | 23376 |
| E2 | Comparative (screw pressed cocoa cake-Sanchez) | 8733 | 5564 | 4836 | 3031 | 1983 | 1099 | 3489 | 361 | 221 | 29318 |
| E3 | Comparative (screw pressed cocoa powder-Sulawesi) | 7104 | 4915 | 3642 | 2020 | 1121 | 576 | 273 | 153 | 66 | 19871 |
| E4 | Comparative (hydraulically pressed cocoa cake-blend of origins) | 7157 | 3981 | 2479 | 1226 | 583 | 260 | 87 | — | — | 15773 |
| E5 | Comparative (hydraulically pressed cocoa powder-blend of origins) | 5811 | 3169 | 1503 | 537 | 171 | 55 | — | — | — | 11245 |
| E6 | (DeZaan defatted cocoa powder — DIS — supercritical fluid extracted — alkalized unknown bean origin) | 581 | 421 | 123 | 35 | — | — | — | — | — | 1161 |
| E7 | Comparative (roasted cocoa nibs — blend of origins) | 2526 | 1551 | 824 | 206 | 77 | 64 | 43 | — | — | 5291 |
| E8 | Comparative (propane extracted cocoa nibs — blend of origins) | 2904 | 1855 | 927 | 239 | 116 | 63 | 37 | — | — | 6140 |
| E9 | Comparative (Javabeans) | 2677 | 2092 | 1645 | 984 | 632 | 378 | 240 | 127 | 93 | 8868 |
| E10 | Comparative (Papua New Guinea beans) | 2856 | 1960 | 1672 | 748 | 318 | 145 | 74 | 36 | — | 7807 |
| E11 | Comparative (Papua New Guinea beans) | 5255 | 3652 | 2402 | 959 | 485 | 261 | 159 | 54 | — | 13228 |
| 937-59 | South Region, Sulawesi Liquor | 1801 | 1205 | 555 | 114 | — | — | — | — | — | 3675 |
| 937-59 | Southeast Region, Sulawesi Liquor | 3891 | 2131 | 1213 | 457 | 150 | 31 | — | — | — | 7873 |
| 937-59 | Central Region, Sulawesi Liquor | 3668 | 1718 | 847 | 265 | 68 | — | — | — | — | 6566 |
| CC 1 | Comparative Screw Press Cake #1 | 2267 | 2034 | 1360 | 579 | 297 | 132 | 50 | 27 | 14 | 6759 |
| CC 2 | Comparative Screw Press Cake #2 | 2894 | 2313 | 1546 | 681 | 323 | 138 | 49 | 35 | 21 | 8001 |
| CC 3 | Comparative Screw Press Cake #3 | 2437 | 1878 | 1231 | 561 | 339 | 88 | 44 | 12 | trace | 6589 |
| CC 4 | Comparative Screw Press Cake #4 | 2520 | 1972 | 1219 | 500 | 240 | 87 | 26 | 10 | 8 | 6581 |
| CM 1 | Press Meal #1 | 1374 | 1246 | 791 | 300 | 122 | 15 | trace | trace | trace | 3848 |
| CM 2 | Press Meal #2 | 2596 | 2287 | 1313 | 459 | 182 | 68 | 7 | trace | trace | 6911 |
| CM 3 | Press Meal #3 | 2389 | 2171 | 1289 | 492 | 186 | 82 | 15 | trace | trace | 6624 |
| WA | West African Press Cake | 2455 | 2073 | 1561 | 757 | 422 | 177 | 107 | 72 | 44 | 7670 |

TABLE 2-continued

Polyphenol Content
Defatted Dry Weight Basis

| | | Oligomer Amount (μg/g) | | | | | | | | Total |
|---|---|---|---|---|---|---|---|---|---|---|
| Sample | Description | Monomer | Dimer | Trimer | Tetramer | Pentamer | Hexamer | Heptamer | Octamer | Nonamer | Polyphenol |

1. CC 1–4 refers to bean pressed with shell
2. CM 1–3 refers to bean pressed with shell (defatted)
3. Oligomer Amounts are rounded to the nearest whole number; total procyanidins may include additional polyphenols above nonamer The sample set containing 9 pressed cocoa cakes, 3 cocoa meals, 3 pressed cocoa powder samples, 3 liquor samples, 3 bean samples and 2 nib samples were analyzed for procyanidin levels by the aforementioned procedure. The results are shown in Table 2 (above). Procyanidin levels were compared-to those previously reported for Sulawesi samples defatted by the inventive process. The screw pressed cocoa cake from Sanchez beans (comparative Sample No. E2) contained procyanidin levels closest to that found in the inventive processed samples, but 30% less total procyanidins. Moreover, the inventive process retained the highest level of higher oligomers, i.e., the level of pentamers from the E2 sample was 1983 ug/g as compared to 3,168 ug/g (sample #937–59) from the inventive process.

Additionally, a sample set containing Sulawesi raw beans prior to processing by the inventive process (RB-1), cocoa bean nibs obtained from the inventive process, according to Example 1, except as modified as discussed below (MN-1), two samples of cocoa solids obtained from the inventive process (MS-120 and MS-150), conventionally processed, Sulawesi raw nibs prior to processing (RN-1 and RN-2), and Sulawesi, conventionally processed cocoa solids (CS-1 and CS-2) were analyzed for procyanidin levels by the aforementioned procedure. The results are shown in Table 3 below. The inventive process was modified at the micronizing stage to adjust the temperature at which polyphenols would be conserved, i.e., approximately 100–110° C.

Polyphenols from inventive solids such as RB-1 and MS-120 can be purified by preparative normal phase chromatography by modifying the method of Rigaud et al., (1993) J. Chrom. 654: 255–260. Separations are affected at ambient temperature on a 5 u Supelcosil LC-Si 100A column (50×2 cm), with an appropriate guard column. Procyanidins are eluted by a linear gradient under the following conditions: (time, %A, %B, flow rate); (0, 92.5, 7.5, 10); (10, 92.5, 7.5, 40); (30, 91.5, 18.5, 40); (145, 88, 22, 40); (150, 24, 86, 40); (155, 24, 86, 50); (180, 0, 100, 50). Prior to use, the mobile phase components can be mixed by the following protocol:

Solvent A preparation (82% methylene chloride, 14% methanol, 2% acetic acid, 2% water):

1. Measure 80 ml of water and dispense into a 4L bottle.
2. Measure 80 ml of acetic acid and dispense into the same 4L bottle.
3. Measure 560 ml of methanol and dispense into the same 4L bottle.
4. Measure 3280 ml of methylene chloride and dispense into the same 4L bottle.
5. Cap the bottle and mix well.
6. Purge the mixture with high purity Helium for 5 to 10 minutes to degas.

Repeat 1 to 6 two times to yield 8 volumes of solvent A.

Solvent B preparation (96% methanol, 2% acetic acid, 2% water):

1. Measure 80 ml of water and dispense into a 4L bottle.
2. Measure 80 ml of acetic acid and dispense into the same 4L bottle.
3. Measure 3840 ml of methanol and dispense into the same 4L bottle.
4. Cap the bottle and mix well.
5. Purge the mixture with high purity helium for 5 to 10 minutes to degas.

Steps 1 to 5 can be repeated to yield four (4) volumes of solvent B. Mobile phase composition can be A=methylene chloride with 2% acetic acid and 2% water; B=methanol with 2% acetic acid and 2% water. The column load can be 0.7 g in 7 ml. Components can be detected by UV at 254 nm.

By this method, procyanidins can be obtained from the inventive solids.

As evidenced by the total procyanidin compositions obtained from RB-1, MN-1, MS-120 and MS-150, the inventive process affords at least 70% conservation, even at least 85% conservation (e.g., 85–89% see MS-150) and as much as at least 95% conservation (e.g., 95–100%; see MS-120) of the procyanidin concentration; whereas, the conventional processes result in approximately (less than 50%) to less than 70% conservation of the procyanidin concentration (see CS-1, CS-2).

Further, RN-1 and RN-2 represent varying concentrations of brown beans (or well fermented beans) in the composition starting material, such that, RN-1 was derived from a bean stock containing approximately 25% brown beans, and RN-2 was derived from a bean stock containing approximately 10% brown beans. As evidenced by the total procyandin concentrations obtained from each of these sources, it is evident that the concentration of brown beans present in the starting bean stock is inversely proportional to the total procyandin concentration that may be obtained from such a source, such that those samples derived from bean stocks containing a high percentage of brown beans will yield a relatively low amount of procyanidin (and conversely, slaty and/or purple beans which are less fermented will yield a relatively high amount of procyanidins).

The percentage fat of each composition in Table 3 was also determined. The inventive process obtains levels of fat which are comparable to that derived from conventional methods.

TABLE 3

Defatted Dry Weight Basis

| Sample | Description | Oligomer Amount (μg/g) | | | | | | | | | Total Polyphenol | % Fat |
|---|---|---|---|---|---|---|---|---|---|---|---|---|
| | | Monomer | Dimer | Trimer | Tetramer | Pentamer | Hexamer | Heptamer | Octamer | Nonamer | | |
| RB-1 | Raw Beans, Sulawesi | 11354 | 5924 | 4643 | 3180 | 2181 | 1143 | 529 | 305 | 165 | 31425 | 48.0 |
| MN-1 | Inventive nibs (RB-1 = starting material) | 13129 | 5909 | 4034 | 2120 | 1334 | 792 | 441 | 160 | 94 | 28014 | 47.1 |
| MS-120 | Inventive solids @ 120 psi (RB-1 = starting material) | 15301 | 6592 | 4447 | 2526 | 1507 | 721 | 360 | 219 | 139 | 31811 | 11.9 |
| MS-150 | Inventive solids @ 150 psi (RB-1 = starting material) | 10025 | 5560 | 4839 | 3245 | 2106 | 1139 | 542 | 284 | 214 | 27955 | 11.1 |
| RN-1 | Raw nibs, Sulawesi | 7976 | 5643 | 5426 | 4185 | 3021 | 1806 | 1150 | 624 | 360 | 30192 | 48.5 |
| CS-1 | Conventional solids, Sulawesi | 10527 | 4887 | 2969 | 1585 | 691 | 267 | 35 | 26 | trace | 20986 | 25.8 |
| RN-2 | Raw nibs, Sulawesi | 12219 | 7635 | 7202 | 5619 | 4014 | 2384 | 1471 | 751 | 406 | 41701 | 47.3 |
| CS-2 | Conventional solids, Sulawesi | 10170 | 4863 | 2802 | 1333 | 254 | 182 | 128 | 37 | 40 | 19811 | 26.3 |

Oligomer amount have been rounded to the nearest whole number; total procyanidin may include additional procyanidins above nonamer.
The total procyanidin amounts for MS-120 represent nearly 100% recovery by inventive process.
The total procyanidin amounts for MS-150 represent nearly 89% recovery by inventive process.

EXAMPLE 3

Cocoa Bean Winnowing Using An Air Fluidized-Bed Density Separator

An air fluidized bed density separator (AFBDS) manufactured by Camas International was tested to determine its effectiveness as a cocoa bean winnower. A blend of beans from West Africa and Central America were heated at about 150° C. for about 4 minutes to loosen the shell and were cracked with a centrifugal bean breaker. The cracked beans were separated by the AFBDS which resulted in a shell in nib level of between 0.29 to 0.99% and a nib in shell level of between 6.7 to 8.7%. Although the shell in nib level was acceptable, it was observed that a significant portion of the nibs in the shell was a result of pieces of nib which remained in the large pieces of shell. The large pieces of shell, resembling cracked eggshells, were conveyed on the top of the separation chamber. These shells typically had large pieces of nib entrapped within them which conveyed the nibs into the shell stream. To reduce this nib loss, a system for decreasing the size of the shell pieces was required which did not also decrease the size of the nibs.

A follow-up trial consisted of screening the flow of material between the second and third chamber of the AFBDS. This material was separated with a vibrating screen with a ⅜th inch screen opening. The screen successfully removed the large pieces of shell from the material with virtually no loss of nibs. The material which passed through the screen was introduced back into the third separation chamber and the shells and nibs were subsequently separated in the chamber. The amount of shell in nib was found to be very low, however there remained a loss of small nib in the shell stream.

To reclaim the nib in shell from the third chamber, another vibrating screen was utilized with a 0.11 inch screen opening size. This screen successfully separated the remaining nib from the shell.

The fourth chamber is typically used to remove heavy impurities such as rocks, stones, etc. As a winnower, this chamber would not be required as the winnower will typically receive material which is free of these materials. In practice, the 5% flow into the fourth chamber would be passed through chamber one and onto chamber two and three.

The following is a summary of the performance of the AFBDS as a winnower:

TABLE 4

Air Fluidized Bed/Vibratory Screen Winnowing Results

| | % of Flow | % Shell in Nib | % Nib in Shell |
|---|---|---|---|
| Chamber 1 | 65 | 0.020 | 0 |
| Chamber 2 | 20.0 | 0.002 | 0 |
| 0.375 in. screen | | | <0.1 |
| Chamber 3 | 9.5 | 0.020 | 0.0 |
| 0.11 inch screen | 0.5 | 0.075 | 0.99 |
| Chamber 4 | 5.0 | 0 | 0 |
| TOTAL | 100 | 0.117 | <1.09 |
| CONVENTIONAL WINNOWING | | 1.75 max, 1.00 typical | range of 4–8% |

% of Nib refers to the amount of the clean nib that was taken out in each chamber As can be seen from the results above, the AFBDS can be used as a winnower and provide separations much finer than conventional winnowing processes. The use of an AFBDS surprisingly meets the FDA requirements for the amount of shell in the nib product, and has a very high yield of nib.

Example 4

Chocolate Composition Using Reduced Fat Cocoa Solids from the Inventive Process A sweet (plain) chocolate was produced from the inventive cocoa solids (according to Example 1, except micronizing was at an IBT of 100 to 110° C., which met the international compositional guidelines published by the Codex Alimentarius commission (Samples N-1, M-2; see Tables 5 and 6). In particular, the cocoa solids (302 g) from the inventive process (reduced fat, approx. 11% fat) were coarsely ground using a Bauermeister lab mill Type UTI to obtain a cocoa powder. The resulting cocoa powder was mixed in a 5 qt. bowl with sugar (235.4 g) and cocoa butter (258 g) using a Kitchen Aid mixer Model KSM5OP. This mixture was next refined (particle size reduced) on a J.H. Day Co. three roll refiner, Model 10×22 at 375 psi to obtain refinings. The refinings were subsequently dry conched in a 1 lb. Z-Blade mixer (C.W. Brabender Instruments, Inc. Type 5300) for 1 hour at 60° C. at a constant speed of 69 rpm to obtain a mixture. Alternatively, the dry conching step was performed at ambient temperature (32° C.) for 1 hour to obtain a mixture. Lecithin (2.4 g) and vanillin (1.2 g) were then added to the mixture and a wet conching step was performed. The wet conching process lasted 45 minutes at 60° C. in order to obtain a homogeneous mass to produce a chocolate. Alternatively, the wet conching step was performed at ambient temperature (32° C.) for 45 minutes to obtain a chocolate. The chocolate was subsequently tempered and molded into 28 g blocks for sensory evaluation, wherein a panel of trained chocolate tasters tasted the samples for evaluation parameters such as flavor (see Table 6). The particle size by micrometer of the final chocolate was 23 microns.

Sweet (plain) chocolates were also produced from conventionally processed cocoa solids (conventional screw press, samples S-1, S-2, S-3; see Tables 5 and 6) from a range of origin countries, i.e., Ivory Coast, Dominican Republic and (Sanchez) Indonesia, to allow for comparison with the inventive process. These cocoa solids were also made into chocolates following the procedure outlined above.

Underfermented beans and previously conventionally de-shelled nibs from the same lot used to produce the inventive cocoa solids were also conventionally processed (conventional roasting to make liquor; sample M-3; see Tables 5 and 6) into sweet (plain) chocolates to allow for comparison with the chocolate from the inventive process. In particular, the beans (800 g) were roasted in a lab scale convection oven (Farberware Turbo Oven, Model 460/5) for 15 minutes at 150° C. to roast the beans. The roasted beans were cracked using a Limprimita cocoa breaker made by John Gordon & Co. The shells were subsequently removed from the nibs using a lab scale winnower made by John Gordon & Co., Catador CC-1. The previously conventionally deshelled nibs were then roasted at 150° C. for 10 minutes in the same lab scale connection oven. The roasted nibs from the beans and the roasted nibs which were previously conventionally deshelled were then combined- and stone milled. Nib milling was achieved using a lab scale stone mill (Probatwerke, Model GLX 15). Sugar (236;4 g) and the milled nibs (also known as liquor) (560.0 g) were subsequently refined on a three roll refiner (J.H. Day Co., Model 10×22) at 275 psi to obtain refinings. The refinings were then dry- conched in a 1 lb. Z-Blade mixer (C.W. Brabender Instruments, Inc. Type 5300) for 1 hour at 60° C. at a constant speed of 69 rpm to obtain a mixture. Lecithin (2.4 g) and vanillin (1.2 g) were then added to the mixture and a wet conching step was initiated. The wet conching process lasted 45 minutes at 60° C. to obtain a homogeneous mass of chocolate. The chocolate was subsequently tempered and molded into 28 g blocks for sensory evaluation as described above. The particle size by micrometer of the final chocolate was 11 microns.

As shown below in Tables 5 and 6, chocolate from solids from the inventive process (Samples M1, M2) were surprisingly high in active procyanidins, and have acceptable flavor characteristics. This is surprising because the active procyanidins were not lost in processing the solids into an edible chocolate; and, because the active procyanidins did not adversely affect flavor.

The skilled artisan, without undue experimentation, from this disclosure and the knowledge in the art, can now readily prepare other chocolate compositions, including without limitation, Standard of Identity (U.S.) and non-standard of identity (U.S.) and reduced fat chocolates, as well as other edible compositions, containing high or conserved concentrations of active procyanidins.

TABLE 5

Defatted Dry Weight Basis

| Sample | Description | Oligomer Amount (µg/g) | | | | | | | | | Total Polyphenol |
|---|---|---|---|---|---|---|---|---|---|---|---|
| | | Monomer | Dimer | Trimer | Tetramer | Pentamer | Hexamer | Heptamer | Octamer | Nonamer | |
| M1 | Inventive Process Sulawesi Cake Heat during conching (60°) | 5904 | 3084 | 2174 | 1251 | 1190 | 445 | 229 | 100 | trace | 14379 |
| M2 | Inventive Process Sulawesi Cake No heat during conching (32°) | 6479 | 3239 | 2281 | 1380 | 1292 | 502 | 260 | 119 | trace | 15552 |
| M3 | Inventive Process Sulawesi Beans Conventional lab roasting and milling (60°) | 6123 | 2623 | 1273 | 455 | 472 | 74 | ND | ND | ND | 11020 |
| S1 | Comparative, Conventional screw press solids — | 2920 | 1503 | 884 | 416 | 327 | 108 | 21 | ND | ND | 6178 |

TABLE 5-continued

Defatted Dry Weight Basis

| Sample | Description | Oligomer Amount (μg/g) | | | | | | | | | Total Polyphenol |
|---|---|---|---|---|---|---|---|---|---|---|---|
| | | Monomer | Dimer | Trimer | Tetramer | Pentamer | Hexamer | Heptamer | Octamer | Nonamer | |
| | Sulawesi Cake Heat during conching (60°) | | | | | | | | | | |
| S2 | Comparative, Conventional screw press solids — Sanchez Cake Heat during conching (60°) | 3782 | 2106 | 1505 | 753 | 571 | 163 | 60 | ND | ND | 8940 |
| S3 | Comparative, Conventional screw press solids — Ivory Coast Cake Heat during conching (60°) | 1708 | 1088 | 750 | 387 | 244 | 56 | ND | ND | ND | 4233 |

TABLE 6

Sensory Evaluation of Plain Chocolate made from inventive solids vs. conventionally processed cocoa solids or beans Flavor characteristics and intensities* (10 cm scale)

| sample | Chocolate/ cocoa | Roast | Fruity/ Floral | Brown Fruit/ Spice | Particle Size | Bitter | Astringent | Woody |
|---|---|---|---|---|---|---|---|---|
| M-1 | 5.4 | 4.2 | 2.6 | — | 2.9 | 6.5 | 5.8 | 2.5 |
| M-2 | 4.6 | 2.8 | 1.5 | 1.7 | 3.4 | 5.9 | 6.6 | 4.2 |
| M-3 | 4.0 | 3.5 | — | 5.1 | 3.3 | 8.0 | 7.2 | 7.8 |
| S-1 | 4.5 | 3.9 | 1.6 | 2.6 | 2.6 | 3.6 | 3.9 | 4.9[a] |
| S-2 | 5.9 | 4.0 | 2.7 | 2.8 | 3.5 | 7.4 | 6.2 | — |
| S-3 | 6.6 | 4.1 | 3.9 | 3.2 | 3.4 | 8.3 | 6.3 | 3.7 |

*Scores represent the average of 9 trained chocolate tasters.
— = stastically insignificant
[a]burnt coffee grounds flavor detected

| Codes | Description |
|---|---|
| M-1 | Inventive Process heat, 120 psi, PTE 3–4/08 |
| M-2 | Inventive Process no heat conching, PTE 3–4/08 |
| M-3 | Nibs, Sulawesi, conventional roast beans, PTE 3–4/08 |
| S-1 | Comparative, conventional screw press solids — Sulawesi |
| S-2 | Comparative, conventional screw press solids — Sanchez |
| S-3 | Comparative, conventional screw press solids — Ivory Coast |

Having thus described in detail the preferred embodiments of the present invention, it is to be understood that the invention defined by the appended claims is not to be limited by particular details set forth in the above descriptions as many apparent variations thereof are possible without departing from the spirit or scope of the present invention.

What we claim is:

1. A food composition comprising partially defatted cocoa solids which are prepared by a method which comprises the steps of:

(a) heating cocoa beans for a time and at an internal bean temperature just sufficient to loosen the cocoa shells without roasting the cocoa nibs;

(b) winnowing the cocoa nibs from the cocoa shells;

(c) screw pressing the cocoa nibs to produce cocoa butter and partially defatted cocoa solids; and (d) recovering the partially defatted cocoa solids, which cocoa solids contain cocoa polyphenols including cocoa procyanidins from the unroasted cocoa nibs.

2. The food composition of claim 1, which is a chocolate-flavored food product.

3. The food composition of claim 1, which is a chocolate food product.

4. The food composition of claim 1, which is a chocolate confectionery.

5. The food composition of claim 1, which is a chocolate-flavored confectionery.

6. The food composition of claim 4, which is an SOI chocolate confectionery.

7. The food composition of claim 4, which is a non-SOI chocolate confectionery.

8. The food composition of claim 7, which is a low fat chocolate.

9. The food composition of claim 1, which is a chocolate drink.

10. The food composition of claim 1, which is a chocolate-flavored drink.

11. The food composition of claim 1, wherein the food product is a chocolate-coated food product.

12. The food composition of claim 11, wherein the chocolate-coated food product contains a caramel, a nougat, a fruit piece, a nut, or a wafer.

13. The food composition of claim 11, wherein the chocolate-coated food product is a chocolate-coated inclusion which contains a cordial cherry or peanut butter.

14. The food composition of claim 11, which is a chocolate-coated dessert.

15. The food composition of claim 11, which is a chocolate-coated ice cream.

16. A dietary composition comprising partially defatted cocoa solids prepared by a method which comprises the steps of:
   a) heating cocoa beans for a time and at an internal bean temperature just sufficient to loosen the cocoa shells without roasting the cocoa nibs;
   b) winnowing the cocoa nibs from the cocoa shells;
   c) screw pressing the cocoa nibs to produce cocoa butter and partially defatted cocoa solids; and
   d) recovering the partially defatted cocoa solids, which cocoa solids contain cocoa polyphenols including cocoa procyanidins from the unroasted cocoa nibs.

17. A therapeutic composition comprising partially defatted cocoa solids prepared by a method which comprises the steps of:
   a) heating cocoa beans for a time and at an internal bean temperature just sufficient to loosen the cocoa shells without roasting the cocoa nibs;
   b) winnowing the cocoa nibs from the cocoa shells;
   c) screw pressing the cocoa nibs to produce cocoa butter and partially defatted cocoa solids; and
   d) recovering the partially defatted cocoa solids, which cocoa solids contain cocoa polyphenols including cocoa procyanidins from the unroasted cocoa nibs.

18. The composition of claims 1, 16 or 17, wherein the cocoa beans are slaty cocoa beans, purple cocoa beans, mixtures of slaty and purple cocoa beans, mixtures of purple and brown cocoa beans, or mixtures of slaty, purple and brown cocoa beans.

19. The composition of claim 18, wherein the cocoa beans are slaty cocoa beans, purple cocoa beans, or mixtures thereof.

* * * * *